(12) United States Patent
Gallou

(10) Patent No.: US 7,375,218 B2
(45) Date of Patent: May 20, 2008

(54) PROCESS FOR PREPARING MACROCYCLIC HCV PROTEASE INHIBITORS

(75) Inventor: Fabrice Gallou, Danbury, CT (US)

(73) Assignee: Boehringer Ingelheim International GmbH, Ingelheim (DE)

(*) Notice: Subject to any disclaimer, the term of this patent is extended or adjusted under 35 U.S.C. 154(b) by 114 days.

(21) Appl. No.: 11/222,950

(22) Filed: Sep. 9, 2005

(65) Prior Publication Data

US 2006/0063916 A1    Mar. 23, 2006

Related U.S. Application Data

(60) Provisional application No. 60/610,709, filed on Sep. 17, 2004.

(51) Int. Cl.
*C07D 215/16* (2006.01)
*C07K 5/08* (2006.01)

(52) U.S. Cl. .................................. 540/456; 546/153
(58) Field of Classification Search ............... 540/460; 546/153
See application file for complete search history.

(56) References Cited

U.S. PATENT DOCUMENTS

| 2003/0181363 A1 | 9/2003 | Llinas-Brunet et al. |
| 2004/0248779 A1 | 12/2004 | Dersch et al. |
| 2005/0049187 A1 | 3/2005 | Brandenburg et al. |
| 2005/0080005 A1 | 4/2005 | Llinas-Brunet et al. |
| 2005/0209135 A1* | 9/2005 | Busacca et al. ............... 514/10 |

FOREIGN PATENT DOCUMENTS

| WO | WO 00/59929 | 10/2000 |
| WO | WO 03/064455 A2 | 8/2003 |
| WO | WO 2004/089974 A1 | 10/2004 |
| WO | WO 2005/028501 A1 | 3/2005 |

OTHER PUBLICATIONS

Mauro Napoletano, et al, The Synthesis and Biological Evaluation of a Novel Series of Phthalazine PDE4 Inhibitors I, Bioorganic & Medicinal Chemistry Letters 10 (2000) 2235-2238.
Frederick J. Brown, et al, Hydroxyacetophenone-Derived Antagonists of the Peptidoleukotrienes, J. Med. Chem. 1989, 32, 807-826.

* cited by examiner

*Primary Examiner*—Bruck Kifle
(74) *Attorney, Agent, or Firm*—Michael P. Morris; Mary-Ellen M. Devlin; Philip I. Datlow

(57) ABSTRACT

Disclosed are highly convergent processes for preparing compounds of formula (I), which compounds are potent active agents for the treatment of hepatitis C virus (HCV) infection:

11 Claims, No Drawings

US 7,375,218 B2

PROCESS FOR PREPARING MACROCYCLIC HCV PROTEASE INHIBITORS

CROSS-REFERENCE TO RELATED APPLICATIONS

This application claims benefit to U.S. Provisional Application No. 60/610,709, filed Sep. 17, 2004.

BACKGROUND OF THE INVENTION

1. Technical Field

The invention relates to an improved process for the preparation of macrocyclic compounds useful as agents for the treatment of hepatitis C viral (HCV) infections.

2. Background Information

The macrocyclic compounds of the following formula (I) and methods for their preparation are disclosed in the following patent applications and publications: Llinas Brunet et al, U.S. Patent Application Publication No. 2005/0080005 A1; Samstag et al, U.S. Patent Application Publication No. 2004/0248779 A1 and Busacca et al, U.S. application Ser. No. 11/078,074, filed Mar. 11, 2005:

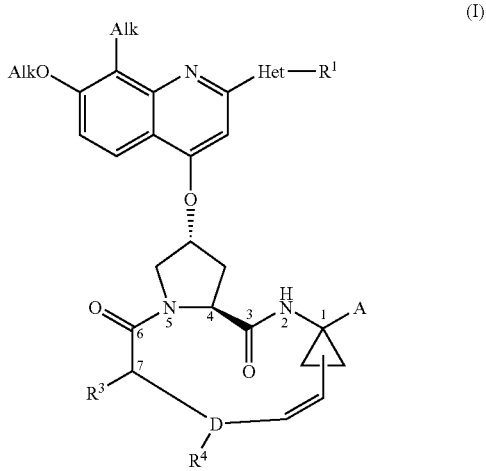

wherein Het is a five-, six- or seven-membered saturated or unsaturated heterocycle containing from one to four heteroatoms selected from nitrogen, oxygen and sulfur; said heterocycle being substituted with $R^1$ at any available position on the heterocycle;

$R^1$ is selected from $R^{20}$, $-NR^{22}COR^{20}$, $-NR^{22}COOR^{20}$ $-NR^{22}R^{21}$ and $-NR^{22}CONR^{21}R^{23}$, wherein $R^{20}$ is selected from $(C_{1-8})$alkyl, $(C_{3-7})$cycloalkyl and $(C_{3-7})$ cycloalkyl$(C_{1-4})$alkyl-, wherein said cycloalkyl or cycloalkylalkyl may be mono-, di- or tri-substituted with $(C_{1-3})$alkyl;

$R^{21}$ is H or has one of the meanings of $R^{20}$ as defined above, $R^{22}$ and $R^{23}$ are independently selected from H and methyl, each Alk is independently a $C_1$-$C_6$ alkyl group;

$R^3$ is hydroxy, $NH_2$, or a group of formula $-NH-R^9$, wherein $R^9$ is $C_6$ or $C_{10}$ aryl, heteroaryl, $-C(O)-R^{10}$, $-C(O)-NHR^{10}$ or $-C(O)-OR^{10}$, wherein $R^{10}$ is $C_{1-6}$ alkyl or $C_{3-6}$ cycloalkyl;

D is a 3 to 7-atom saturated alkylene chain;

$R^4$ is H, or from one to three substituents at any carbon atom of said chain D, said substituent independently selected from the group consisting of: $C_{1-6}$ alkyl, $C_{1-6}$ haloalkyl, $C_{1-6}$ alkoxy, hydroxy, halo, amino, oxo, thio, or $C_{1-6}$ thioalkyl; and A is an amide of formula $-C(O)-NH-R^{11}$, wherein $R^{11}$ is selected from the group consisting of: $C_{1-8}$ alkyl, $C_{3-6}$ cycloalkyl, $C_6$ or $C_{10}$ aryl, $C_{7-16}$ aralkyl and $SO_2R^{11A}$ wherein $R^{11A}$ is $C_{1-8}$ alkyl, $C_{3-7}$ cycloalkyl or $C_{1-6}$ alkyl-$C_{3-7}$ cycloalkyl;

or A is a carboxylic acid or a pharmaceutically acceptable salt or ester thereof;

The compounds of formula (I) are disclosed in the above-mentioned patent documents as being active agents for the treatment of hepatitis C viral (HCV) infections and can be used for said treatment indication as described therein. The problem addressed by the present invention is to provide highly convergent processes which allow for the manufacture of these compounds with a minimum number of steps and with sufficient overall yield.

BRIEF SUMMARY OF THE INVENTION

The process provided by the present invention, as described herein, is highly convergent and this convergency manifests itself in a much shorter synthetic sequence leading to the compounds of Formula (I). The process of the present invention provides for the preparation of Formula (I) via a coupling reaction between an advanced macrocyclic intermediate compound of formula (IX) and a compound of formula QUIN:

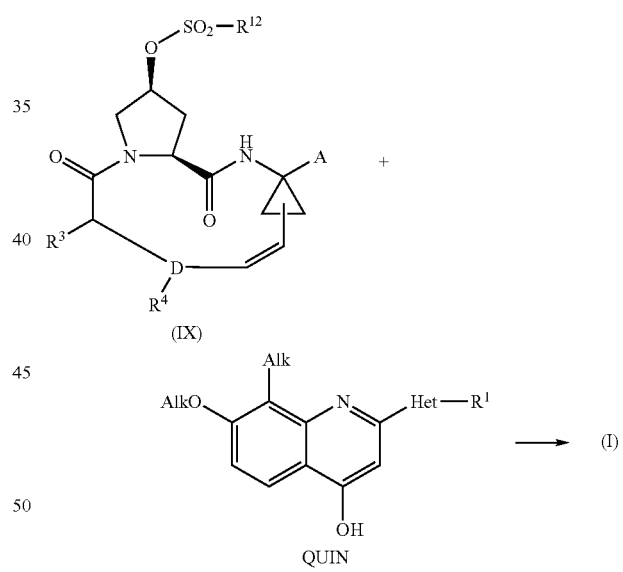

The present invention is therefore directed to a multi-step synthetic process for preparing compounds of formula (I) using the synthetic sequences as described herein; particular individual steps of this multi-step process; and particular individual intermediates used in this multi-step process.

DETAILED DESCRIPTION OF THE INVENTION

Definition of Terms and Conventions Used

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, $(C_{1-8})$alkyl means an alkyl group or radical having 1 to 8 carbon atoms and $(C_{3-7})$cycloalkyl means a cycloalkyl group having from 3 to 7 carbon atoms in the ring. In general, for groups comprising two or more subgroups, the last named group is the radical attachment point, for example, "cycloalkylalkyl" means a monovalent radical of the formula cycloalkyl-alkyl- and phenylalkyl means a monovalent radical of the formula phenyl-alkyl-. Unless otherwise specified below, conventional definitions of terms control and conventional stable atom valences are presumed and achieved in all formulas and groups.

The term "alkyl" as used herein, either alone or in combination with another substituent, means acyclic, straight or branched chain alkyl substituents containing the specified number of carbon atoms.

The term "alkoxy" as used herein, either alone or in combination with another substituent, means an alkyl group as defined above linked as a substituent through an oxygen atom: alkyl-O—.

In general, all tautomeric forms and isomeric forms and mixtures, whether individual geometric isomers, stereoisomers, optical isomers or racemic or non-racemic mixtures of isomers, of a chemical structure or compound are intended, unless the specific stereochemistry or isomeric form is specifically indicated in the compound name or structure.

The term "pharmaceutically acceptable salt" as used herein includes those derived from pharmaceutically acceptable bases. Examples of suitable bases include choline, ethanolamine and ethylenediamine. $Na^+$, $K^+$, and $Ca^{++}$ salts are also contemplated to be within the scope of the invention (also see *Pharmaceutical Salts*, Birge, S. M. et al., J. Pharm. Sci., (1977), 66, 1-19, incorporated herein by reference).

The term "pharmaceutically acceptable ester" as used herein, either alone or in combination with another substituent, means esters of the compound of formula I in which any of the carboxylic acid functions of the molecule is replaced by an alkoxycarbonyl function:

in which the R moiety of the ester is selected from alkyl (e.g. methyl, ethyl, n-propyl, t-butyl, n-butyl); alkoxyalkyl (e.g. methoxymethyl); alkoxyacyl (e.g. acetoxymethyl); aralkyl (e.g. benzyl); aryloxyalkyl (e.g. phenoxymethyl); aryl (e.g. phenyl), optionally substituted with halogen, $C_{1-4}$ alkyl or $C_{1-4}$ alkoxy. Other suitable prodrug esters are found in *Design of Prodrugs*, Bundgaard, H. Ed. Elsevier (1985) incorporated herewith by reference. Such pharmaceutically acceptable esters are usually hydrolyzed in vivo when injected in a mammal and transformed into the acid form of the compound of formula I. With regard to the esters described above, unless otherwise specified, any alkyl moiety present advantageously contains 1 to 16 carbon atoms, particularly 1 to 6 carbon atoms. Any aryl moiety present in such esters advantageously comprises a phenyl group. In particular the esters may be a $C_{1-16}$ alkyl ester, an unsubstituted benzyl ester or a benzyl ester substituted with at least one halogen, $C_{1-6}$ alkyl, $C_{1-6}$ alkoxy, nitro or trifluoromethyl.

The following chemicals may be referred to by these abbreviations:

| Abbreviation | Chemical Name |
|---|---|
| BOC | tert-butoxycarbonyl |
| DABCO | 1,4-diazabicyclo[2.2.2]octane |
| DBU | 1,8-Diazabicyclo[5.4.0]undec-7-ene |
| DCC | 1,3-Dicyclohexylcarbodiimide |
| DCHA | Dicyclohexylamine |
| DIPEA or DIEA | Diisopropylethylamine or Hünigs-Base |
| DMAP | Dimethylaminopyridine |
| DMF | N,N-Dimethylformamide |
| DMSO | Dimethylsulfoxide |
| DMTMM | 4-(4,6-Dimethoxy-1,3,5-triazin-2-yl)-4-methylmorpholinium Chloride |
| EDC | 1-(3-dimethylaminopropyl)-3-ethylcarbodiinide hydrocholide |
| HATU | O-(7-azabenzotriazol-1-yl)-N,N,',N'-tetramethyluronium hexafluorophosphate |
| HBTU | O-Benzotriazol-1-yl-N,N,',N'-tetramethyluronium hexafluorophosphate |
| HOAT | 1-Hydroxy-7-azabenzotriazole |
| HOBT | 1-Hydroxybenzotriazole |
| KDMO | Potassium 3,7-dimethyl-3-octanoxide |
| MCH | Methylcyclohexane |
| MIBK | 4-Methyl-2-pentanone |
| MTBE | Methyl, tert-butyl ether |
| NMP | 1-Methyl-2-pyrrolidinone |
| SEH | Sodium 2-ethylhexanoate |
| TBTU | O-(Benzotriazol-1-yl)-N,N,N',N'-tetramethyluronium tetrafluoroborate |
| THF | Tetrahydofuran |

EMBODIMENTS OF THE INVENTION

In the synthetic schemes below, unless specified otherwise, all the substituent groups in the chemical formulas shall have the same meanings as in the Formula (I). The reactants used in the synthetic schemes described below may be obtained either as described herein, or if not described herein, are themselves either commercially available or may be prepared from commercially available materials by methods known in the art. Certain starting materials, for example, may be obtained by methods described in the International Patent Applications WO 00/09543, WO 00/09558, WO 00/59929, U.S. Pat. No. 6,323,180 B1 and U.S. Pat. No. 6,608,027 B1.

Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Typically, reaction progress may be monitored by High Pressure Liquid Chromatography (HPLC), if desired, and intermediates and products may be purified by chromatography on silica gel and/or by recrystallization.

I. Preparation of QUIN Starting Material

In one embodiment, the present invention is directed to the following general multi-step synthetic method for preparing the intermediate compounds of formula QUIN, as set forth in Scheme I below, as well as the individual steps and intermediates set forth therein:

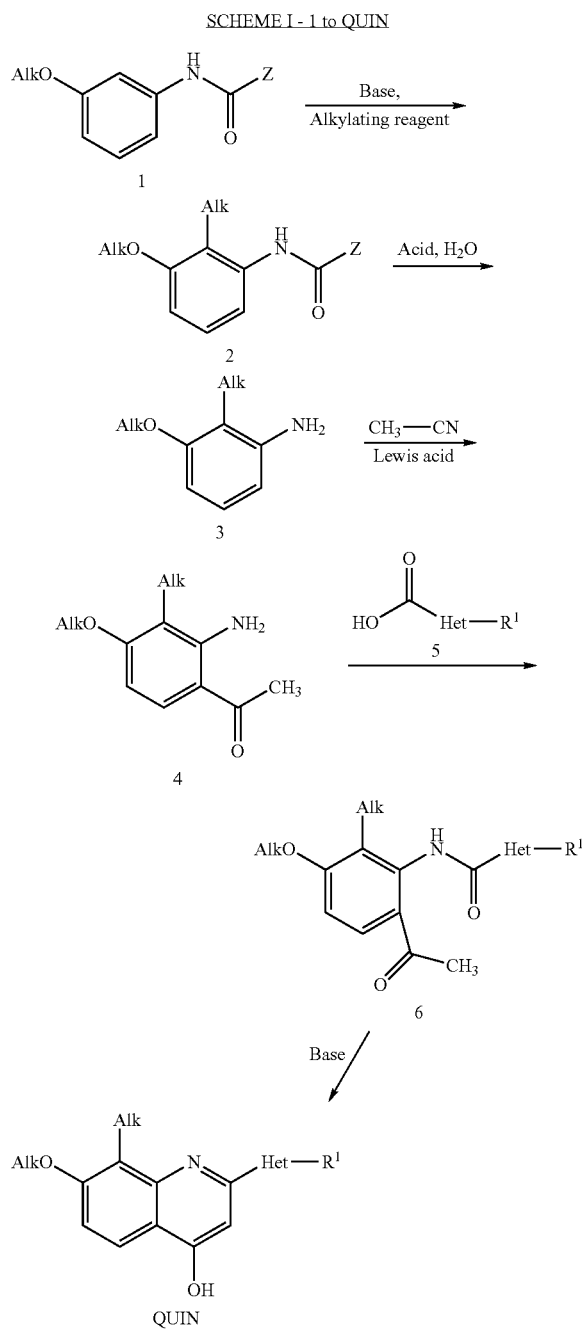

SCHEME I - 1 to QUIN wherein each Alk is independently a $C_1$-$C_6$ alkyl group, Z is tert-butyl or t-butyl-oxy, and $R^1$ and Het in this and subsequent schemes are as defined for Formula I.

In the first step, a compound of formula 1 is treated with a base and a alkylating agent to obtain compound 2. The general requirements for this step are the use of a base of strength sufficient to form the desired dianion. This could be any alkyllithium, a metalloamide such as lithium diisopropylamide (LDA), lithium tetramethylpiperidide (LiTMP), a metallohexamethyldisilazide such as KHMDS, LiHMDS or NaHMDS, an organozincate, a metal alkoxide in a cation-solvating solvent such as DMSO, a magnesium base such as a Grignard reagent, and the like. The preferred bases would be n-butyllithium and LDA. Other protected anisidines could likely be used such as the N-BOC derivative, or other amides such as N-methyl, N-ethyl, etc. Any organic solvent that does not interfere with the dianion formation could be used, such as THF, alkyl-THF's, dioxane, alkanes, cycloalkanes, dialkylethers such as MTBE, cyclopentylmethylether, dibutylether, and the like. The preferred solvents would be THF, alkyl-THF's and alkanes. The temperature for the dianion formation could be between −100° C. and 25° C., with the preferred range between −30° C. and 25° C. Alternatively, directed metalation (e.g. with Pd) could be used to functionalize the aniline to a trisubstituted aromatic ring. In such case, the aniline could be protected as before or even left unprotected. The temperature range could be increased to 100° C.

The alkylating agent can be any suitable alkyl electrophile such as methyl bromide, methyl chloride, methyl iodide, methyl sulfonate, dimethyl sulfate, methyl carbonate. Once the dianion has been generated in a suitable solvent, the alkylating agent could be added neat or in solution, or alternatively the dianion could be added to the alkylating agent either neat or in solution. The preferred mode would be to add the dianion slowly to the alkylating agent in solution. The temperature for the alkylation could be between −100° C. and 25° C., with the preferred range between −30° C. and 25° C.

In the next step, compound 2 is hydrolyzed by treatment with an aqueous acid mixture to obtain 3. Any aqueous acid mixture could be used such as water with trifluoroacetic acid, a chloroacetic acid such as trichloroacetic acid, a sulfonic acid such as methanesulfonic acid, hydrochloric acid, sulfuric acid, nitric acid, phosphoric acid, a strong acid resin such as DOWEX 50, and the like. The preferred acids would be hydrochloric acid and sulfuric acid in 2-12 M concentration, preferably at least 6M. Co-solvents that are miscible with water could also be used, such as alcohols like ethanol, isopropanol, or ethers such as DME, diglyme, and the like. The hydrolysis could be carried out between 0° C. and 200° C., with the preferred temperature between 0° C. and 100° C.

In the next step, compound 3 is treated with an alkylated nitrile (Alk-CN) and a Lewis acid (Sugasawa acylation) to obtain compound 4. For the conversion of 3 to 4, Lewis acids by themselves or in combination, could be used, such as $AlCl_3$, $BCl_3$, $GaCl_3$, $FeCl_3$ and mixtures thereof, and the like. The preferred method would be to use $BCl_3$ with $AlCl_3$. Any solvent which will not be easily acylated could be used such as halocarbons, halobenzenes, alkylbenzenes such as toluene, and alkylnitriles such as acetonitrile, with the preferred solvents being 1,2-dichloroethane, chlorobenzene and toluene. The reaction temperature could be between 0° C. and 150° C., preferably between 25° C. and 75° C. The Sugasawa acylation can be carried out using either the free base or HCl salt of the aniline 3. The Friedel-Crafts acylation may also be used to prepare the ketoamide. An alternate synthesis would be to hydrolyze the pivalamide with aqueous acid first, then perform the Sugasawa acylation to furnish the tetrasubstituted aniline.

In the next step, compound 4 is acylated with compound 5 to obtain compound 6. For the conversion of 4 to 6, acylation could be achieved by either first converting carboxylic acid 5 to an activated form, such as an acid chloride, using a suitable activating agent, or by using standard peptide coupling protocols. The preferred method would be to create the acid chloride of compound 5 using oxalyl chloride or thionyl chloride. This activated species would then be coupled with aniline 4 in any organic solvent or in water, using an added base. The preferred solvents would be THF and the preferred base triethylamine. The reaction temperature could be between −30° C. and 150° C., preferably between −20° C. and 50° C.

In the next step, compound 6 is cyclized in the presence of a base to obtain compound QUIN. For the conversion of 6 to QUIN as shown in Scheme I, any base capable of forming the enolate could be used, such as t-BuOK, t-BuONa, t-BuOLi, t-BuOCs, KDMO, LDA, and the like, with t-BuOK and KDMO being preferred. Any organic solvent which does not react with the enolate could be used, such as THF, dioxane, DMSO, DME, NMP and the like, with DME, DMSO and NMP being preferred. The cyclization could be performed at any temperature between 25° C. and 150° C., with 50° C. to 100° C. being preferred.

II. Preparation of Formula IX Starting Material

The macrocyclic starting material of formula IX is prepared by the multi-step sequence set forth below, as also described in U.S. Patent Application Publication No. 2005/0049187 A1:

Step (i)

This step is directed to a process for preparing a compound of formula (IV):

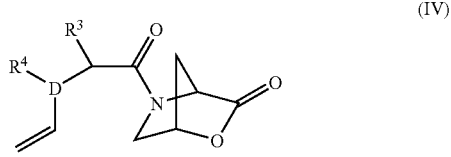

said process comprising:

reacting a compound of formula (II), or a salt thereof, with a compound of formula (III):

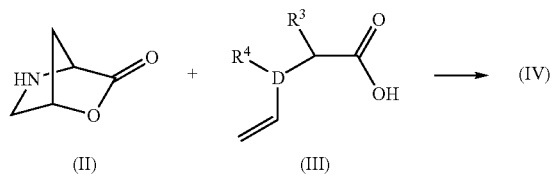

Peptide coupling between compounds of formula (II) and (III) could be obtained under a variety of suitable peptide coupling conditions known in the art, e.g., using conventional peptide coupling reagents such as DCC, EDC, TBTU, HBTU, HATU, DMTMM, HOBT, or HOAT in aprotic solvents such as dichloromethane, chloroform, DMF, NMP, DMSO.

In a specific embodiment, the compound of formula (II) is used in the form of its mesylate salt.

The cyclic lactone of formula (II), used as starting material can be obtained from a commercially available 4-hydroxyproline compound of formula (XI) using standard techniques as outlined in the following general scheme:

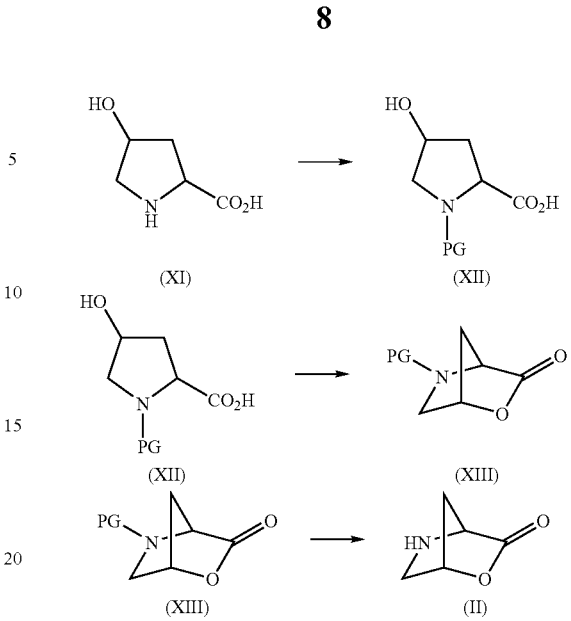

In the first step, an appropriate amino-protecting group (PG) is introduced onto the ring nitrogen atom of the 4-hydroxyproline compound of formula (XI) using conventional procedures. For example, compound of formula (XI) may be dissolved in a suitable solvent and reacted with an appropriate amino-protecting group introducing reagent. For example, and not intending to be limited in its scope, when Boc (tert-butyloxycarbonyl) is the desired protecting group, compound (XI) is reacted with the anhydride $Boc_2O$ (or Boc-ON) in a solvent mixture such as Acetone/Water, MIBK/Water, THF/Water to which a base such as NaOH, KOH, LiOH, triethyl amine, diisopropylethylamine, or N-methyl-pyrrolidine is added, the reaction being carried out at a temperature between 20-60° C.

In the second step, the protected 4-hydroxyproline compound of formula (XII) is converted to the cyclic lactone compound of formula (XIII) by reaction with an appropriate cyclizing reagent in a suitable solvent. In one embodiment, the OH functionality of the compound of formula (XII) is first reacted with a sulfonyl chloride (such as methanesulfonyl chloride, p-toluenesulfonyl choride, or trifluoromethanesulfonyl chloride) in a non-protic solvent (such as THF, dioxane, dichloromethane, chloroform, N-methylpyrrolidone, dimethyl sulfoxide, dimethylformamide, acetone, or methylisobutylketone) in the presence of a tertiary amine base (such as N-methyl-pyrrolidine, diisopropylethylamine or triethylamine) to render a compound with a suitable leaving group, followed by cyclization of the obtained compound in a polar non-protic solvent (such as dioxane) in the presence of a tertiary amine base to give the desired cyclic lactone of formula (XIII).

In the third step, the cyclic lactone compound of formula (XIII) is deprotected using conventional deprotection techniques, for example if BOC is the protecting group, by heating compound of formula (XIII, PG=BOC)) in a suitable solvent in the presence of an acid such as p-toluenesulfonic acid, HCl, HBr, HI, HF, $H_2SO_4$, $H_3PO_4$, methanesulfonic acid or trifluoroacetic acid, to obtain the compound of formula (II).

The compound of formula (II) may optionally be converted into a salt form by reaction with an appropriate acid. A specific example of the preparation of the mesylate salt of the compound of formula (II) starting from an appropriate 4-hydroxyproline compound of formula (XI) is found in the Synthetic Examples section below.

The substituted acid compound of formula (III) used as a starting material may be obtained from commercially available materials using the techniques described in International Patent Application WO 00/59929.

Step (ii)

Step (ii) is directed to a process for preparing a compound of formula (VI):

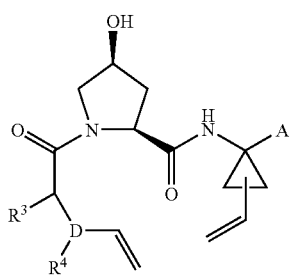

said process comprising:
reacting a compound of formula (IV) with a compound of formula (V):

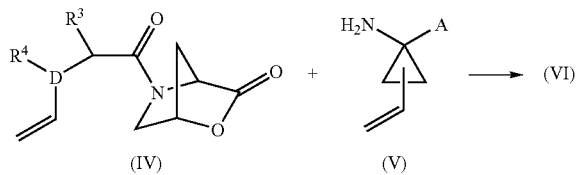

A mixture of a compound of formula (IV), a compound of formula (V) and a suitable base, such as sodium 2-ethylhexanoate (SEH), in a suitable solvent (such as water, toluene, pyridine, a suitable solvent mixture such as toluene/THF or a suitable biphasic solvent system such as water/toluene) is stirred at a temperature from about 20° C. to about 80° C. until completion of the reaction. For work-up the organic layer may be washed and the product isolated after removing the solvent.

The compound of formula (V) used as starting material may be obtained from commercially available materials using the techniques described in International Patent Applications WO 00/59929, WO 00/09543, WO 00/09558 and U.S. Pat. No. 6,323,180 B1.

Step (iii)

Step (iii) is directed to a process for preparing a compound of formula (VIII):

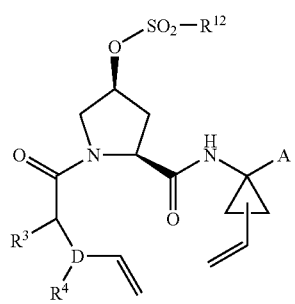

said process comprising:
reacting a compound of formula (VI) with a compound of formula (VII):

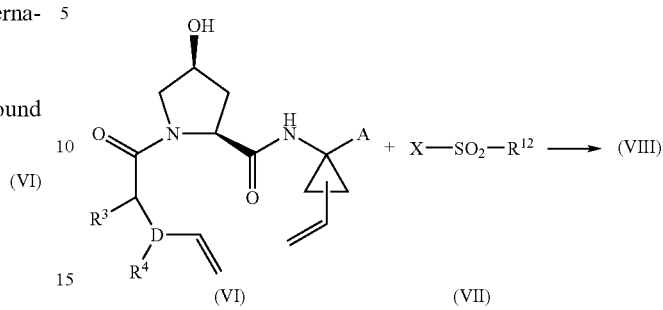

wherein X represents a suitable leaving group and $R^{12}$ is selected from p-tolyl, p-bromophenyl, p-nitrophenyl, methyl, trifluoromethyl, perfluorobutyl and 2,2,2-trifluoroethyl;

To a mixture of compound of formula (VI) and an organic base (such as DABCO, triethylamine, 1-methylpyrrolidine or pyridine) in an organic solvent (such as ether, dicholoromethane, cholorform or toluene), a solution of the compound of formula (VII) is added and the resultant mixture is stirred at ambient temperature (15-25° C.) until completion of reaction.

Step (iv)

Step (iv) is directed to a process for preparing a compound of formula (IX):

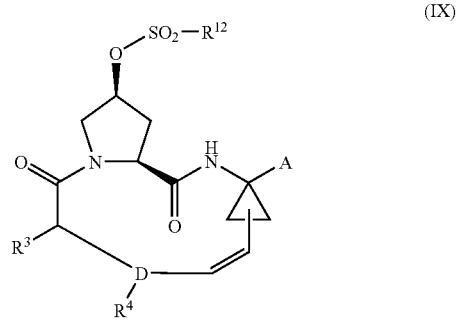

said process comprising cyclyzing a diene compound of formula VIII in the presence of a suitable catalyst:

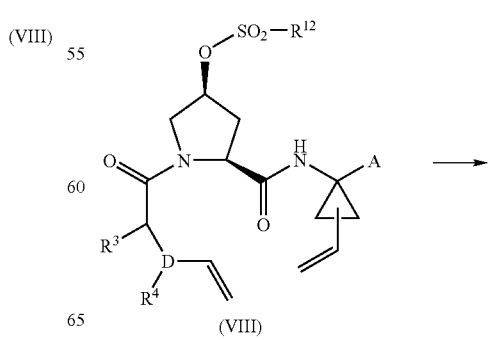

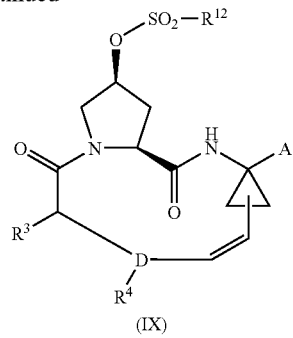

(IX)

Suitable ring-closing catalysts for this step include, for example, ruthenium based catalysts used in olefin metathesis reactions, such as the catalysts described in WO 00/59929.

Specific examples of suitable ruthenium-based catalysts include Grubb's catalyst (first and second generation), Hoveyda's catalyst (first and second generation) and Nolan's catalyst. In a specific embodiment, the catalyst used in this ring-closing step is a compound of formula (XIV):

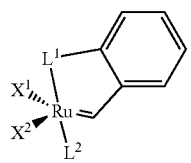

(XIV)

wherein $X^1$ and $X^2$ each independently represent a covalently bonded ligand, $L^1$ represents a ligand which is coordinatively bonded to the ruthenium atom and may be covalently bonded to the phenyl group, and $L^2$ represents a ligand which is coordinatively bonded to the ruthenium atom.

In a particular embodiment of this step, the compound of formula (VIII) is dissolved in a degassed organic solvent (such as toluene or dichloromethane) to a concentration below about 0.02M, then treated with a ruthenium-based catalyst such as the compound of formula (XIV), at a temperature from about 40° C. to about 110° C. until completion of the reaction. Some or all of the ruthenium metal may be removed from the reaction mixture by treatment with a suitable heavy metal scavenger, such as THP or other agents known to scavenge heavy metals. The reaction mixture is washed with water, followed by partial concentration of the organic solution (e.g., by a distillation process). The organic solution may be decolorized, such as by the addition of activated charcoal with subsequent filtration, and then is added to a suitable solvent at a suitable temperature, such as pre-cooled methylcyclohexane, which causes precipitation of the product compound of formula (IX) that is collected by filtration.

III. Preparation of Products of Formula I

In another embodiment, the present invention is directed to a process for preparing the compound of formula (I):

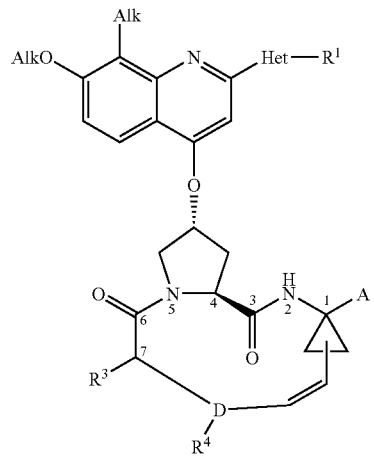

(I)

said process comprising reacting a macrocyclic compound of formula (IX) with a compound of formula QUIN:

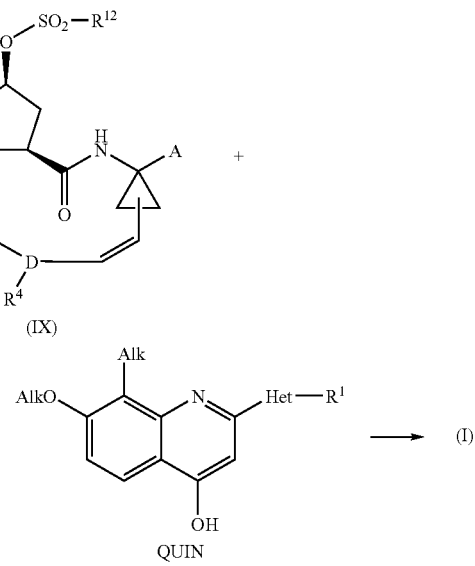

and when A is a carboxylic acid ester group in the resulting compound of formula (I), optionally subjecting the compound of formula (I) to hydrolysis conditions to obtain a compound of formula (I) wherein A is a carboxylic acid group;

and when A is a carboxylic acid group in the resulting compound of formula (I), optionally coupling this compound with a sulfonamide of formula $R^{11A}SO_2NH_2$ in the presence of a suitable coupling agent, such as TBTU or HATU, to obtain a compound of formula (I) wherein A is —C(O)—NH—$SO_2R^{11A}$.

Compounds of formula (IX) and QUIN are mixed in a polar non-protic organic solvent (such as THF, dioxane, dichlormethane, chloroform, N-methylpyrrolidone, dimethyl sulfoxide, dimethylformamide, acetone, or methylisobutylketone) in the presence of an inorganic or organic base (such as cesium carbonate, or DBU) at 40° C. to 100° C. until completion of the reaction. Aqueous workup followed by crystallization from a suitable solvent such as ethyl acetate-heptane or ethyl acetate/methylcyclohexane provides the compounds of formula (I).

When A is a carboxylic acid ester group in formula (I), the esterified compound of formula (I) can optionally be subjected to hydrolysis conditions to obtain the corresponding free carboxylic acid compound. Hydrolysis can be carried out using conventional hydrolysis conditions known in the art. In a particular embodiment, for example, the esterified compound of formula (I) is dissolved in an organic solvent such as THF, and a suitable hydrolyzing agent such as lithium hydroxide monohydrate (LiOH·H$_2$O) is added followed by the addition of water. The resultant solution is stirred at a temperature from about 35° C. to about 50° C. At the end of the reaction, the solution is cooled, and the organic layer collected. A suitable solvent such as ethanol is added to the organic layer and the pH is adjusted to from about pH 5 to about pH 6. The mixture is then warmed to a temperature from about 40° C. to about 50° C. at which point water is added and solution is stirred whereupon the compound of formula (I) begins to precipitate. Upon completion of the precipitation, the solution is cooled to ambient temperature and the compound of formula (I) is collected by filtration, washed and dried.

IV. Preferred Embodiments of the Compound of Formula (I)

The compounds that may be prepared by the processes of the present invention are compounds of the formula (I) as previously set forth, i.e. compound of the following formula:

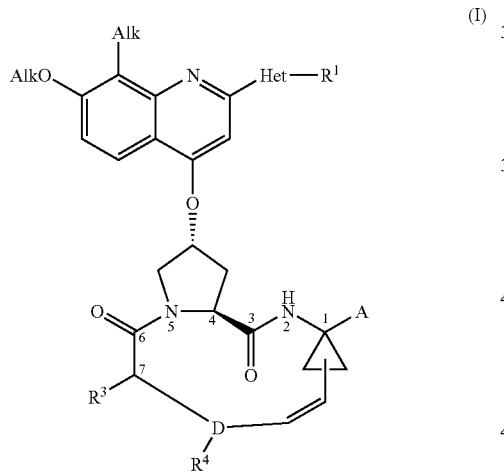

wherein Het is a five-, six- or seven-membered saturated or unsaturated heterocycle containing from one to four heteroatoms selected from nitrogen, oxygen and sulfur; said heterocycle being substituted with $R^1$ at any available position on the heterocycle;

$R^1$ is selected from $R^{20}$, —$NR^{22}COR^{20}$, —$NR^{22}COOR^{20}$, —$NR^{22}R^{21}$ and $NR^{22}CONR^{21}R^{23}$, wherein $R^{20}$ is selected from $(C_{1-8})$alkyl, $(C_{3-7})$cycloalkyl and $(C_{3-7})$cycloalkyl$(C_{1-4})$alkyl-, wherein said cycloalkyl or cycloalkylalkyl may be mono-, di- or tri-substituted with $(C_{1-3})$alkyl;

$R^{21}$ is H or has one of the meanings of $R^{20}$ as defined above, $R^{22}$ and $R^{23}$ are independently selected from H and methyl, each Alk is independently a $C_1$-$C_6$ alkyl group;

$R^3$ is hydroxy, NH$_2$, or a group of formula —NH—$R^9$, wherein $R^9$ is $C_6$ or $C_{10}$ aryl, heteroaryl, —C(O)—$R^{10}$, —C(O)—NHR$^{10}$ or —C(O)—OR$^{10}$, wherein $R^{10}$ is $C_{1-6}$ alkyl or $C_{3-6}$ cycloalkyl;

D is a 3 to 7-atom saturated alkylene chain;

$R^4$ is H, or from one to three substituents at any carbon atom of said chain D, said substituent independently selected from the group consisting of: $C_{1-6}$ alkyl, $C_{1-6}$ haloalkyl, $C_{1-6}$ alkoxy, hydroxy, halo, amino, oxo, thio, or $C_{1-6}$ thioalkyl;

A is an amide of formula —C(O)—NH—$R^{11}$, wherein $R^{11}$ is selected from the group consisting of: $C_{1-8}$ alkyl, $C_{3-6}$ cycloalkyl, $C_6$ or $C_{10}$ aryl, $C_{7-16}$ aralkyl and SO$_2$R$^{11A}$ wherein $R^{11A}$ is $C_{1-8}$ alkyl, $C_{3-7}$ cycloalkyl or $C_{1-6}$ alkyl-$C_{3-7}$ cycloalkyl; and or A is a carboxylic acid or a pharmaceutically acceptable salt or ester thereof;

In a particular embodiment of the compounds of formula (I), the cyclopropyl moiety is selected from the 2 different diastereoisomers where the 1-carbon center of the cyclopropyl has the R configuration as represented by structures (i) and (ii):

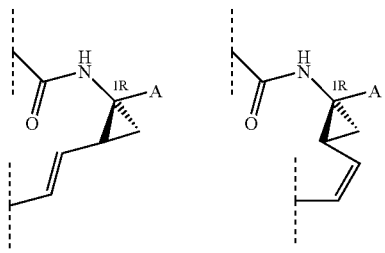

syn to the amide (i), or syn to the A group (ii).

In one specific embodiment of the compounds of formula (I), the olefin group is in the configuration syn to the A group as represented by structure (ii) above.

In another specific embodiment of the compounds of formula (I):

Het-$R^1$ is selected from the following:

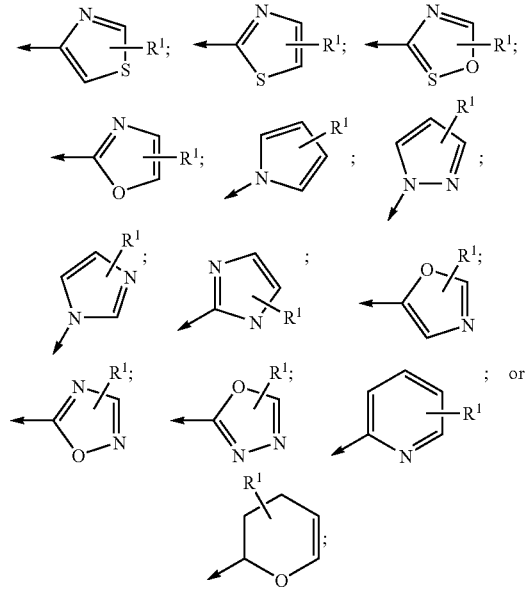

wherein $R^1$ is H, $C_{1-6}$ alkyl, NH—$R^{21}$, NH—C(O)—$R^{20}$, NH—C(O)—NH—$R^{21}$, wherein each $R^{20}$ and $R^{21}$ is independently: $C_{1-6}$ alkyl, or $C_{3-6}$ cycloalkyl;

or $R^1$ is NH—C(O)—OR$^{20}$, wherein $R^{20}$ is $C_{1-6}$ alkyl;

each Alk is independently a $C_1$-$C_4$ alkyl group;
$R^3$ is NH—C(O)—$R^{10}$, NH—C(O)—O$R^{10}$ or NH—C(O)—N$R^{10}$, wherein in each case $R^{10}$ is $C_{1-6}$ alkyl, or $C_{3-6}$ cycloalkyl; and
D is a 4 to 6-atom saturated alkylene chain;
$R^4$ is H or $C_{1-6}$ alkyl;
and A is a carboxylic acid or a pharmaceutically acceptable salt or ester thereof.

In another specific embodiment of the compounds of formula (I), the olefin group is in the configuration syn to the A group as represented by structure (ii) above;

Het-$R^1$ is

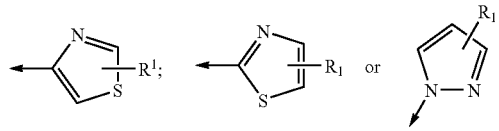

wherein $R^1$ is NH—$R^{21}$ or NH—C(O)—$R^{20}$, wherein $R^{20}$ and $R^{21}$ are independently: $C_{1-6}$ alkyl, or $C_{3-6}$ cycloalkyl;
each Alk is independently a $C_1$-$C_3$ alkyl group;
$R^3$ is NH—C(O)—O$R^{10}$, wherein $R^{10}$ is $C_{1-6}$ alkyl, or $C_{3-6}$ cycloalkyl;
$R^4$ is H or $C_{1-6}$ alkyl;
D is a 5-atom saturated alkylene chain; and
A is a carboxylic acid or a pharmaceutically acceptable salt or ester thereof.

Examples of specific compounds falling within the scope of formula (I) that may be prepared by the processes of the present invention are set forth in Llinas Brunet et al, U.S. Patent Application Publication No. 2005/0080005 A1 and Samstag et al, U.S. Patent Application Publication No. 2004/0248779 A1, both herein incorporated by reference.

I claim:
1. A process for preparing a compound of formula (I):

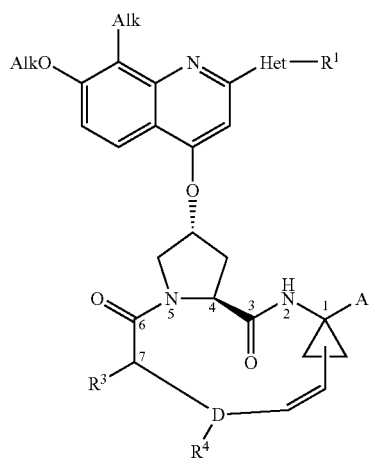

(I)

wherein Het is a five-, six- or seven-membered saturated or unsaturated heterocycle containing from one to four heteroatoms selected from nitrogen, oxygen and sulfur; said heterocycle being substituted with $R^1$ at any available position on the heterocycle;
$R^1$ is selected from H, $R^{20}$, —N$R^{22}$CO$R^{20}$, —N$R^{22}$COO$R^{20}$, —N$R^{22}$N$R^{21}$ and —N$R^{22}$CON$R^{21}R^{23}$, wherein $R^{20}$ is selected from $(C_{1-8})$alkyl, $(C_{3-7})$cycloalkyl and $(C_{3-7})$ cycloalkyl$(C_{1-4})$alkyl-, wherein said cycloalkyl or cycloalkylalkyl may be mono-, di- or tri-substituted with $(C_{1-3})$alkyl;
$R^{21}$ is H or has one of the meanings of $R^{20}$ as defined above,
$R^{22}$ and $R^{23}$ are independently selected from H and methyl,
each Alk is independently a $C_1$-$C_6$ alkyl group;
$R^3$ is hydroxy, $NH_2$, or a group of formula —NH—$R^9$, wherein $R^9$ is $C_6$ or $C_{10}$ aryl,
heteroaryl, —C(O)—$R^{10}$, —C(O)—NH$R^{10}$ or —C(O)—O$R^{10}$,
wherein $R^{10}$ is $C_{1-6}$ alkyl or $C_{3-6}$ cycloalkyl;
D is a 3 to 7-carbon atom saturated alkylene chain;
$R^4$ is H, or from one to three substituents at any carbon atom of said chain D, said substituent independently selected from the group consisting of: $C_{1-6}$ alkyl, $C_{1-6}$ haloalkyl, $C_{1-6}$ alkoxy, hydroxy, halo, amino, oxo, thio, or $C_{1-6}$ thioalkyl; and
A is an amide of formula —C(O)—NH—$R^{11}$, wherein $R^{11}$ is selected from the group consisting of: $C_{1-8}$ alkyl, $C_{3-6}$ cycloalkyl, $C_6$ or $C_{10}$ aryl, $C_{7-16}$ aralkyl and $SO_2R^{11A}$ wherein $R^{11A}$ is $C_{1-8}$ alkyl, $C_{3-7}$ cycloalkyl or $C_{1-6}$ alkyl-$C_{3-7}$ cycloalkyl;
or A is a carboxyl group or a pharmaceutically acceptable salt thereof;
or A is a pharmaceutically acceptable ester group of the formula

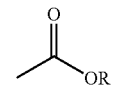

in which the R moiety of the ester is selected from alkyl; alkoxyalkyl; alkoxyacyl: aralkyl; aryloxyalkyl; and aryl; each optionally substituted with halogen, $C_{1-4}$ alkyl or $C_{1-4}$ alkoxy;
said process comprising reacting a macrocyclic compound of formula (IX) with a compound of formula QUIN to obtain a compound of formula (I):

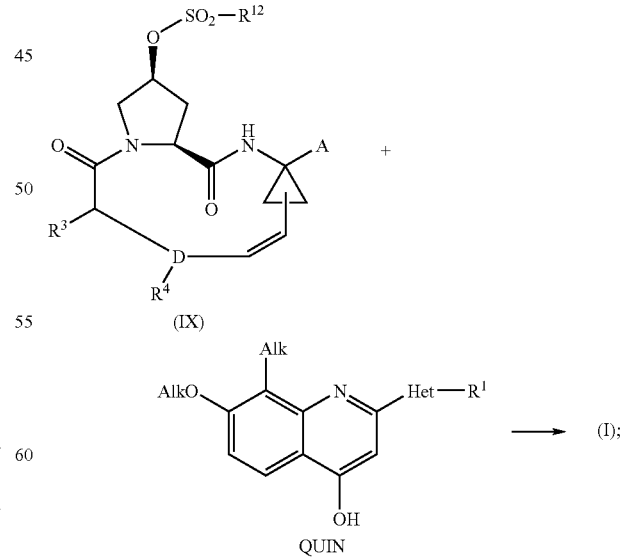

and when A is a pharmaceutically acceptable ester group in the resulting compound of formula (I), optionally subjecting the compound of formula (I) to hydrolysis conditions to obtain a compound of formula (I) wherein A is a carboxyl group;

and when A is a carboxyl group in the resulting compound of formula (I), optionally coupling this compound with a sulfonamide of formula $R^{11A}SO_2NH_2$ in the presence of a suitable coupling agent to obtain a compound of formula (I) wherein A is —C(O)—NH—$SO_2R^{11A}$.

2. A process according to claim 1, wherein the compounds of formula (IX) and QUIN are mixed in a polar non-protic organic solvent in the presence of an inorganic or organic base and at a temperature of 40° C. to 100° C.

3. A process according to claim 2, wherein the solvent is selected from THF, dioxane, dicholormethane, chloroform, N-methylpyrrolidone, dimethyl sulfoxide, dimethylformamide, acetone and methylisobutylketone.

4. A process according to claim 2, wherein the base is selected from cesium carbonate and DBU.

5. A process according to claim 1, wherein:
Het-$R^1$ is selected from the following:

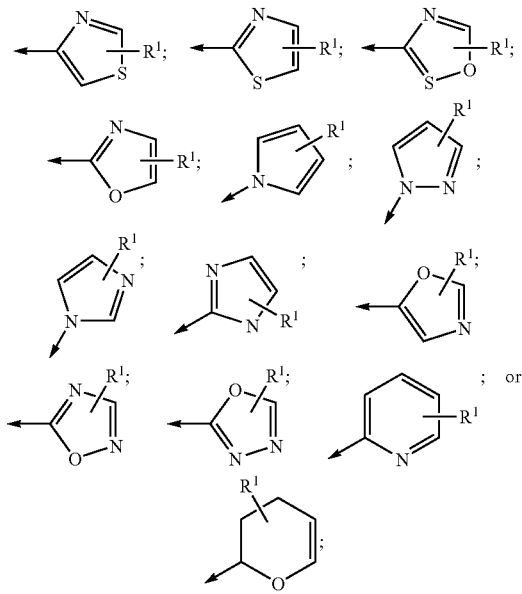

wherein $R^1$ is H, $C_{1-6}$ alkyl, NH—$R^{21}$, NH—C(O)—$R^{20}$, NH—C(O)—NH—$R^{21}$, wherein each $R^{20}$ and $R^{21}$ is independently: $C_{1-6}$ alkyl, or $C_{3-6}$ cycloalkyl;

or $R^1$ is NH—C(O)—$OR^{20}$, wherein $R^{20}$ is $C_{1-6}$ alkyl;

each Alk is independently a $C_1$-$C_4$ alkyl group;

$R^3$ is NH—C(O)—$R^{10}$, NH—C(O)—$OR^{10}$ or NH—C(O)—$NR^{10}$, wherein in each case $R^{10}$ is $C_{1-6}$ alkyl, or $C_{3-6}$ cycloalkyl; and D is a 4 to 6-carbon atom saturated alkylene chain;

$R^4$ is H or $C_{1-6}$ alkyl;

and A is a carboxyl group or a pharmaceutically acceptable salt thereof or a pharmaceutically acceptable ester group as defined in claim 1.

6. A process according to claim 1, wherein:
the olefin group is in the configuration syn to the A group as represented by structure below:

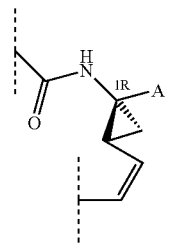

olefin syn to the A group;
Het-$R^1$ is

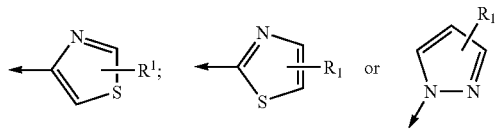

wherein $R^1$ is NH—$R^{21}$ or NH—C(O)—$R^{20}$, wherein $R^{20}$ and $R^{21}$ are independently: $C_{1-6}$ alkyl, or $C_{3-6}$ cycloalkyl;

each Alk is independently a $C_1$-$C_3$ alkyl group;

$R^3$ is NH—C(O)—$OR^{10}$, wherein $R^{10}$ is $C_{1-6}$ alkyl, or $C_{3-6}$ cycloalkyl;

$R^4$ is H or $C_{1-6}$ alkyl;

D is a 5-carbon atom saturated alkylene chain; and

A is a carboxyl group or a pharmaceutically acceptable salt thereof or a pharmaceutically acceptable ester group as defined in claim 1.

7. A compound of formula 6:

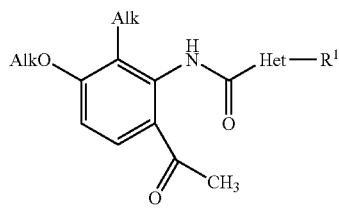

wherein each Alk is independently a $C_1$-$C_6$ alkyl group;

Het is a five-, six- or seven-membered saturated or unsaturated heterocycle containing from one to four heteroatoms selected from nitrogen, oxygen and sulfur; said heterocycle being substituted with $R^1$ at any available position on the heterocycle; and $R^1$ is selected from H, $R^{20}$, —$NR^{22}COR^{20}$, —$NR^{22}COOR^{20}$—$NR^{22}R^{21}$ and —$NR^{22}CONR^{21}R^{23}$, wherein $R^{20}$ is selected from $(C_{1-8})$alkyl, $(C_{3-7})$cycloalkyl and $(C_{3-7})$cycloalkyl$(C_{1-4})$alkyl-, wherein said cycloalkyl or cycloalkylalkyl may be mono-, di- or tri-substituted with $(C_{1-3})$alkyl;

$R^{21}$ is H or has one of the meanings of $R^{20}$ as defined above, and $R^{22}$ and $R^{23}$ are independently selected from H and methyl.

8. A process for preparing a compound of formula 6 according to claim 7, said process comprising acylating a compound of formula 4 with a compound of formula 5 to obtain a compound of formula 6, wherein Alk, Het and $R^1$ are as defined in claim 7:

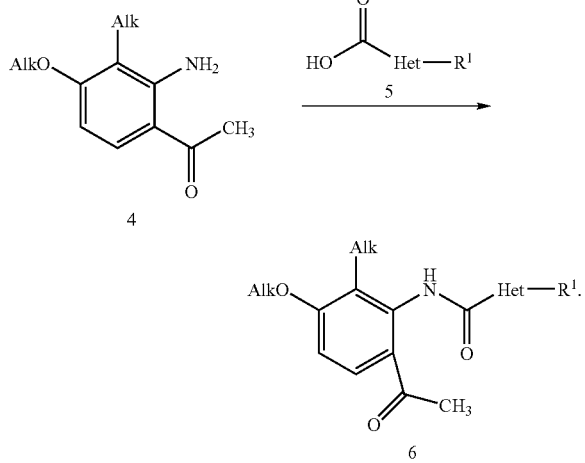

9. A compound of formula QUIN:

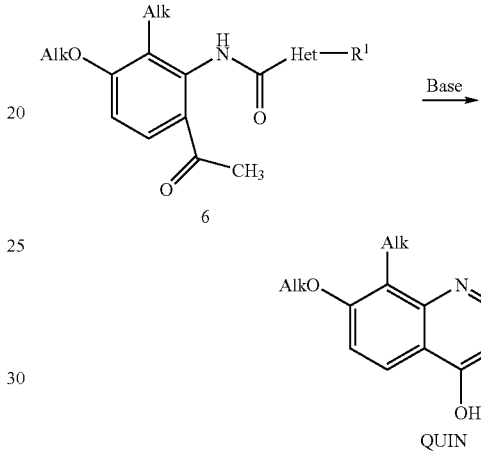

wherein each Alk is independently a $C_1$-$C_6$ alkyl group;
Het is a five-, six- or seven-membered saturated or unsaturated heterocycle containing from one to four heteroatoms selected from nitrogen, oxygen and sulfur; said heterocycle being substituted with $R^1$ at any available position on the heterocycle; and
$R^1$ is selected from H, $R^{20}$, —$NR^{22}COR^{20}$, —$NR^{22}COOR^{20}$—$NR^{22}R^{21}$ and —$NR^{22}CONR^{21}R^{23}$, wherein $R^{20}$ is selected from $(C_{1-8})$alkyl, $(C_{3-7})$cycloalkyl and $(C_{3-7})$cycloalkyl$(C_{1-4})$alkyl-, wherein said cycloalkyl or cycloalkylalkyl may be mono-, di- or tri-substituted with $(C_{1-3})$alkyl;

$R^{21}$ is H or has one of the meanings of $R^{20}$ as defined above, and $R^{22}$ and $R^{23}$ are independently selected from H and methyl.

10. A process for preparing a compound of formula QUIN according to claim 9, said process comprising cyclizing the compound of formula 6 in the presence of a base to obtain a compound of formula QUIN, wherein Alk, Het and $R^1$ are as defined in claim 9:

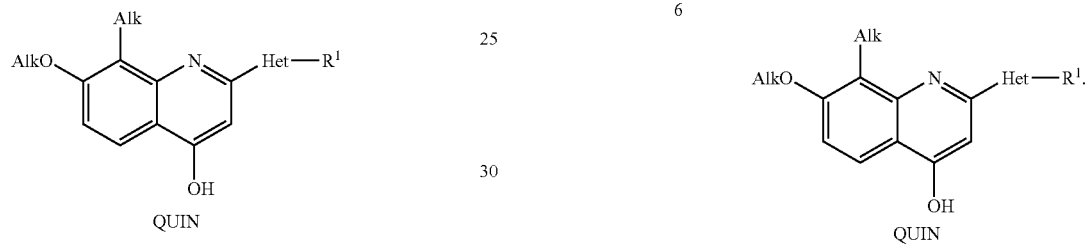

11. The process of claim 1, wherein a compound of formula (I) wherein A is a carboxyl group is coupled with a sulfonamide of formula $R^{114}SO_2NH_2$ in the presence of a suitable coupling agent selected from TBTU or HATU to obtain a compound of formula (I) wherein A is —(O)—NH-$SO_2R^{114}$.

* * * * *